United States Patent
Greenbank et al.

(10) Patent No.: US 6,823,041 B2
(45) Date of Patent: Nov. 23, 2004

(54) GRASPING SYSTEM FOR AUTOMATED EXCHANGE OF ELONGATED SAMPLES IN AN X-RAY ANALYSIS APPARATUS

(75) Inventors: Michael Geoffrey Holmes Greenbank, Irlam (GB); Andrew Martin Watts, Congleton (GB); Peter John Hardman, Stockport (GB); Karl-Eugen Mauser, Bietigheim (DE)

(73) Assignee: Bruker AXS GmbH, Karlsruhe (DE)

( * ) Notice: Subject to any disclaimer, the term of this patent is extended or adjusted under 35 U.S.C. 154(b) by 196 days.

(21) Appl. No.: 10/214,127

(22) Filed: Aug. 8, 2002

(65) Prior Publication Data

US 2003/0048871 A1 Mar. 13, 2003

(30) Foreign Application Priority Data

Sep. 7, 2001 (DE) ......................................... 101 43 990

(51) Int. Cl.[7] .......................................... G01N 23/223
(52) U.S. Cl. ............................. 378/44; 378/79; 378/208
(58) Field of Search .............................. 378/44–49, 79, 378/208

(56) References Cited

U.S. PATENT DOCUMENTS

| | | |
|---|---|---|
| 4,669,771 A | 6/1987 | Finneran |
| 5,147,522 A | 9/1992 | Sarrine |
| 5,216,243 A * | 6/1993 | Varjonen et al. ............ 250/328 |

FOREIGN PATENT DOCUMENTS

| | | |
|---|---|---|
| DE | 23 24 255 | 11/1974 |
| DE | 35 12 459 | 10/1986 |
| DE | 43 19 061 | 12/1993 |
| DE | 198 03 477 | 9/1999 |
| DE | 198 51 501 | 9/2000 |
| EP | 0 867 724 | 9/1998 |
| WO | WO 93/ 20612 | 10/1993 |

OTHER PUBLICATIONS

"Spectrometry Solutions; s4 Explorer", Bruker AXS Analytical X–Ray Systems GmbH, Karlsruhe, 2001 1 page only.

Sprys, J–W., "Specimen Holder for Energy Dispersive X–ray Analysis in the Transmission Electron Microscope", Rev. Sci. Instrum., vol. 46, No. 5, Jun. 1975.

* cited by examiner

*Primary Examiner*—Craig E. Church
(74) *Attorney, Agent, or Firm*—Paul Vincent

(57) ABSTRACT

An X-ray analysis apparatus for investigating material samples, comprising a device for automatic exchange of the samples (1), which comprises a gripping device (4) for precise removal of any desired sample (1) from a depositing position (3) and for transfer into a transfer and/or measuring position and back to a depositing position (3), wherein at least some of the samples are surrounded by a sample holder (13;13') in the peripheral direction, is characterized in that the samples or containers containing the samples project past the sample holder in the vertical z direction perpendicular to the horizontal x-y plane and that the gripping device is disposed and structured on a side of the sample to surround parts of a sample or of a sample container which project past the sample holder in an operating position in the z direction and to grasp the sample holder. This allows, with minor and technically simple modifications, automatic processing of a plurality of samples in an X-ray analysis apparatus of this type including samples which are considerably elongated in the z direction.

11 Claims, 2 Drawing Sheets

GRASPING SYSTEM FOR AUTOMATED EXCHANGE OF ELONGATED SAMPLES IN AN X-RAY ANALYSIS APPARATUS

This application claims Paris Convention priority of DE 101 43 990.3 filed Sep. 7, 2001 the complete disclosure of which is hereby incorporated by reference.

BACKGROUND OF THE INVENTION

The invention concerns an X-ray analysis apparatus for investigating sample materials having a device for automatic exchange of the samples which comprises a gripping device for precise removal and return of any desired sample from and back to a deposition position and for transferral into a transfer and/or measuring position, wherein at least some of the samples are surrounded, in the peripheral direction, by a sample holder.

An X-ray analysis apparatus of this type is known e.g. from the company leaflet "SPECTROMETRY SOLUTIONS; S4 EXPLORER", Bruker AXS Analytical X-Ray Systems GmbH, 2001.

This document provides a detailed description of the functional principles of an arrangement of this type. Such X-ray analysis apparatus are used in laboratories and research institutes for rapid, routine, and non-destructive analyses of the most differing of sample materials. X-ray fluorescence methods, X-ray diffractometry, or other X-ray analysis methods can be used for examining the material samples. The material samples may be massive solid bodies, powder, or liquid samples disposed in appropriate sample containers.

Analysis devices of this type are provided for routine, rapid examination of a large number of samples. For this reason, an automatic exchange device must be provided for transporting, within the device, each of a plurality of samples to be examined. The known devices comprise a sample table for receiving the samples which is immovably fixed in the apparatus as e.g. described in the above-cited company leaflet. This sample table has openings defining an m×n matrix for inserting the different samples or sample containers. These are filled manually with the different samples according to a plan determined by the user before starting a measuring series which subsequently runs automatically without further manual influence on the part of the user.

Towards this end, the X-ray analysis apparatus comprises a gripping device for precise removal of any desired sample from one of the depositing positions, transfer into a transfer or measuring position and for return back into the depositing position. To be able to address all positions on the rigid, rectangular sample table, the gripping device drive mechanics must be relatively complicated. The gripping robot must be movable in both the x and y directions.

The samples or sample containers of an X-ray analysis apparatus of this type are usually dimensioned in the z direction to end flush with the upper edge of the sample holder where the gripping device engages (see e.g. DE 198 51 501 C1). The sample-sided part of the gripping device thereby abuts the upper edge of the sample and of the sample holder during the gripping process.

Samples which extend in the z direction, e.g. containers with sample liquid or rod-shaped solid body samples, cannot be automatically moved with the gripping device of this system. Up to now, such samples had to be individually, manually inserted into the measuring position. Routine investigation of a plurality of samples has not been previously possible with such elongated samples using the conventional arrangement of gripping device and sample holder.

In contrast thereto, it is the underlying purpose of the invention to propose an X-ray analysis apparatus having the above-mentioned features which also permits automatic processing of a plurality of samples in an X-ray analysis device of this type using as simple and as few technical means as possible and with samples of considerable extension in the z direction.

SUMMARY OF THE INVENTION

This object is achieved in accordance with the invention in a surprisingly simple and effective fashion in that the samples or containers holding the samples project past the sample holder in the direction of a vertical z direction extending perpendicular to the horizontal x-y plane, wherein the gripping device is disposed and structured on a side of the sample to surround the parts of a sample or of a sample container projecting, in the z direction, past the sample holder in an operating position to grasp the sample holder.

Modification of an X-ray analysis apparatus of this type is thereby possible with means which are technically easy to realize to facilitate processing of samples extended in the z direction, e.g. liquid containers. This design also facilitates loading and unloading of a sample holder with such extended samples. Moreover, this grasping system can easily grasp conventional samples thereby allowing universal use of the invention for the most differing types of samples. Previously, difficult special solutions had to be found for samples extended in the z direction. The above embodiment of the invention permits standardization of a very simple sample holder and use thereof at little expense.

In a particularly preferred embodiment of the invention, the sample holder comprises one (or several) holding section(s) disposed adjacent to the bottom-sided end of the sample or of a sample container to engage behind the sample or the container holding the sample in a plane which is parallel to the x-y plane for forming a mechanical stop in the z direction for the sample or the sample container. This further facilitates loading the sample holder with the sample to obtain a defined, final position in the z direction.

The holding section is preferably annular to provide full peripheral contact of the sample when fitting into the sample holder. For samples with flat bottoms, surface contact is thereby achieved. For samples with a bulged bottom, e.g. a test tube, at least circular contact is provided to guarantee a defined z position of the sample relative to the sample holder.

The sample holder usually surrounds the sample annularly, preferably circularly, on its side facing the gripping device during operation. The sample or the sample container can then either be inserted or pressed into the sample holder ring.

In a further development of the invention, the sample holder comprises several parallel rods extending in the z direction which surround the sample in the peripheral direction on its side facing the gripping device during operation. This facilitates centering of the sample and extension of the rods in the z direction also provides a certain flexibility for deflection in the x-y plane during insertion of the sample to prevent damage to the sample due to excessive loading during pressing into the sample holder.

A further development is also advantageous wherein the parallel rods are disposed on the upper side of the annular holding section facing the gripping device during operation. The sample holder is thereby formed by the annular holding section and the rods disposed thereon which extend in the z direction.

Instead of the annular structure on the side of the sample, in embodiments of the invention, the gripping device can comprise at least three parallel rods which are preferably distributed uniformly about the periphery of the sample to be held and which extend in the z direction.

In embodiments of the invention, the gripping device can be operated mechanically. Although a gripping robot of this type is simple and inexpensive to manufacture, it is not very compact and does require significant amounts of space. In particular, relatively large amounts of space are usually required in the horizontal x-y plane for a mechanical gripping process. The depositing positions of the samples on the sample table in these embodiments must consequently have corresponding mutual separations to ensure safe gripping of the samples in the sample holder without contacting neighboring samples.

Alternatively or additionally, the gripping device can be operated pneumatically, preferably through suctioning the sample holders by underpressure. A pneumatically actuated mechanical gripper is also possible with which the pneumatic gripping suctioning process must be carried out only at locations with particularly little space. In this case, the pneumatic device may serve both parts of the gripping system.

In a further development of this embodiment, the gripping device comprises rod-shaped gripping elements disposed on the side of the sample (as in an above-mentioned embodiment), wherein at least some of the parallel rods extending in the z direction can define suction nozzles for suctioning parts of the sample holder. In any case, an arrangement of this type requires considerably less space than a mechanical gripping arrangement since the parallel rods must not deflect in the x-y plane during the gripping process but can be rigidly lowered onto the sample holder in the z direction.

Embodiments of the invention are particularly preferred with which the gripping device is operated magnetically. Although a magnetic means of this type is usually more expensive than a mechanical means, it can be designed much more compactly.

In most of these embodiments, the gripping device is an electromagnet which can be externally controlled with electrical currents for activating and deactivating the gripping process.

In other further developments of this embodiment, the gripping device can have permanent magnetic sections on its side facing the sample holder during operation. A magnetic gripping device of this type is somewhat less demanding than an electromagnet, however a device for mechanical displacement of the permanent magnetic sections in the z direction must be provided for separating the grasped sample when depositing into the respective target position.

In a particularly preferred further development of the invention, the sample holder is formed at least partially of magnetizable, preferably ferromagnetic material on its side facing the gripping device during operation such that attraction and gripping thereof by means of a magnetic gripping device is particularly simple.

Finally, another advantageous further development of the invention provides that the annular holding section consists of plastic material into which ferromagnetic rods, extending in the z direction, are inserted on the side of the sample holder facing the gripping device during operation between which the sample or a container containing the sample can be received. An arrangement of this type can be produced and handled at relatively low cost.

A sample holder having the above-described properties and a gripping device with the inventive modifications for use in an X-ray analysis apparatus of the inventive type are also within the scope of the invention.

Further advantages can be extracted from the drawings and the description. The features mentioned above and below can be used in accordance with the invention either individually or collectively in any arbitrary combination. The embodiments shown and described are not to be understood as exhaustive enumeration, rather have exemplary character for describing the invention.

The invention is shown in the drawings and is explained in more detail by means of embodiments.

DESCRIPTION OF THE PREFERRED EMBODIMENT

Figure 1:
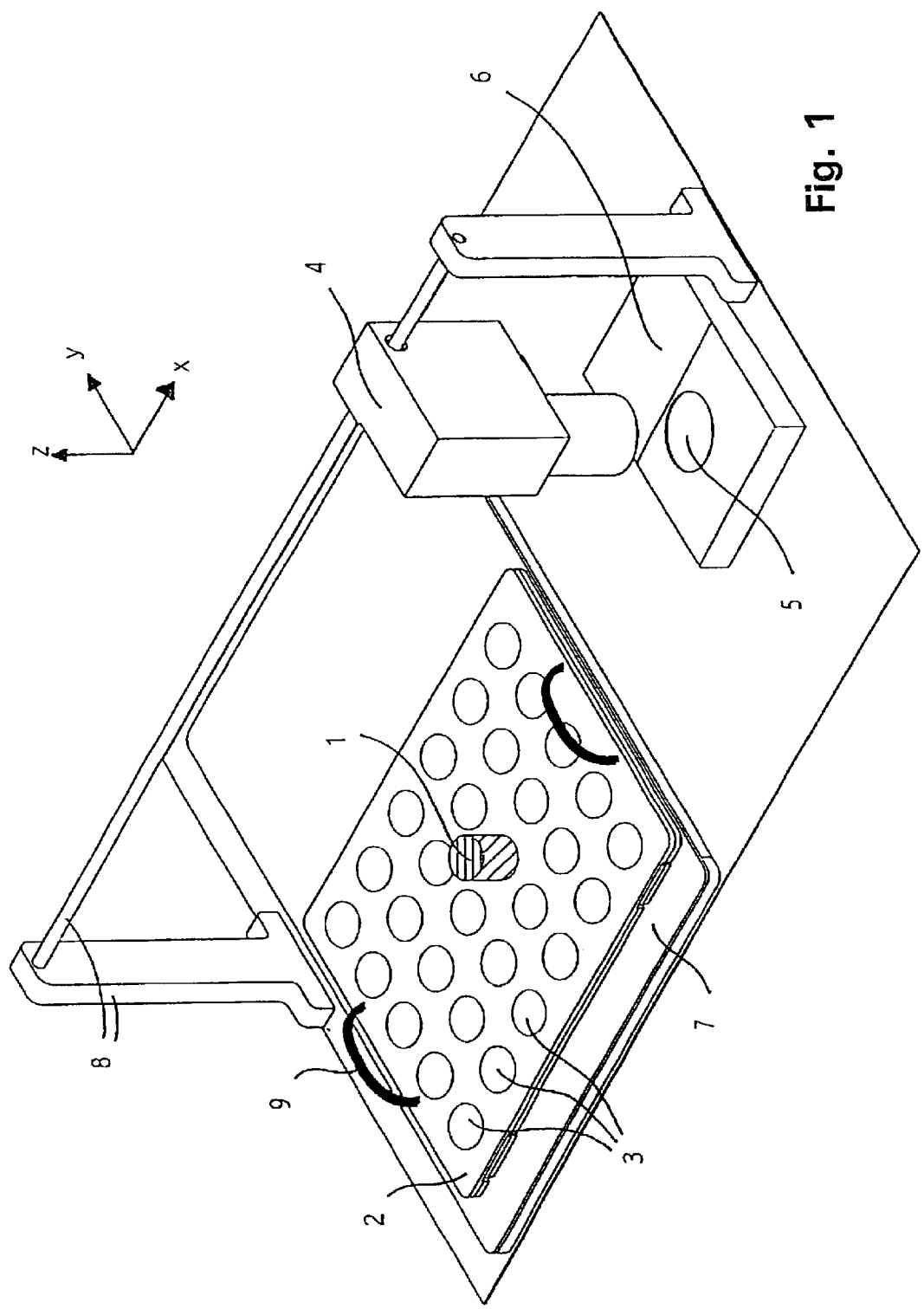
FIG. 1 schematically shows the gripping device of the linearly displaceable sample table and of the measuring position in an inventive X-ray analysis apparatus.

FIG. 1 schematically shows part of the "innards" of an inventive X-ray analysis apparatus. The one single sample 1 on a sample table 2 represents a plurality of samples to be examined. The sample table 2 has depositing positions 3 disposed like a matrix in m lines, each of which can be provided with a sample.

A gripping device 4 is provided for precise removal of any desired sample 1 from a depositing position 3 in the sample table 2 and for transfer of the removed sample 1 to a measuring position 5. To protect the environment from X-ray radiation during operation, the measuring position 5 can be covered during the measurement by a radiation-shielding slider 6.

The gripping device 4 can be displaced on a frame 8 in the x direction along one of the m lines for access to any individual depositing position 3 in the sample table 2. The sample table 2 can be displaced linearly at a right angle thereto in the y direction on a rail plate 7. The sample table 2 is removably disposed on the rail plate 7 such that the samples 1 can also be inserted manually into the depositing positions 3 from outside of the inventive X-ray analysis apparatus. The embodiment shown comprises two handles 9 for removing the sample table 2 from the apparatus.

Figure 2:
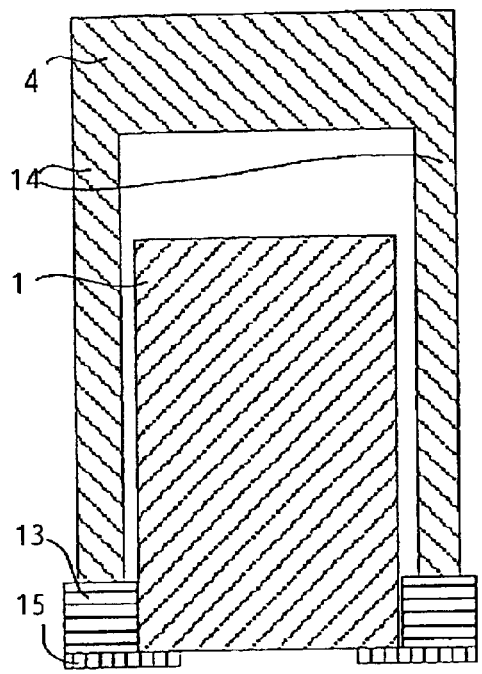
FIG. 2 schematically shows a horizontal section through a gripping device in accordance with the invention comprising a sample which is fitted into an inventive annular sample holder.

FIG. 2 schematically shows a vertical section through an inventive gripping device 4 having rods 14 which laterally grasp about a sample 1 of pronounced elongation in the z direction, and is moved against a sample holder 13 annularly surrounding the sample 1. The bottom side of the sample holder 13 is connected to an annular holding section 15 which engages under the sample 1 and acts as a mechanical stop for the sample 1 in the z direction.

For gripping the sample holder 13 with the fitted sample 1, the rods 14 of the gripping device 4 can comprise magnets and the sample holder 13 can be magnetizable, preferably comprising permanent magnetic material. The gripper 4 can thereby be an electromagnet or a permanent magnet.

Figure 3:
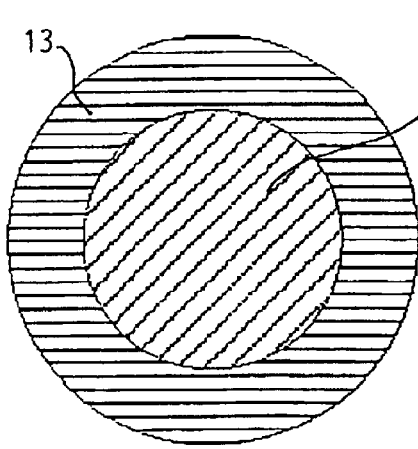
FIG. 3 shows a top view onto the sample with sample holder in accordance with FIG. 2.

Alternatively, the rods 14 of the gripping device 4 can define a suction nozzle for suctioning parts of the sample holder 13 annularly surrounding the sample 1 (FIG. 3).

Instead of rods 14, the gripping device 4 can have a tube-shaped end on the side of the sample, which must have an inside diameter larger than the outer diameter of the parts of the sample 1 projecting past the holding device 13 in the z direction. The tube-shaped end of the gripping device 4 can then be displaced in the z direction over the sample 1 to grip the sample holder 13.

Figure 4:
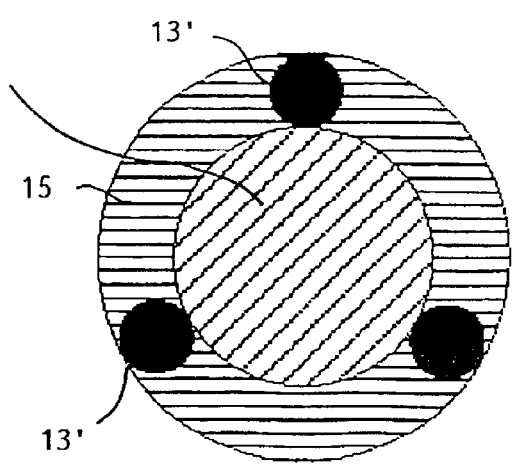
FIG. 4 shows a top view onto a sample with rod-shaped sample holder and annular holding section.

As an alternative to the sample holder 13 shown in FIG. 3, a sample holder 13' can be provided (FIG. 4) having parallel rods extending in the z direction between which the sample 1 fits. As shown in the embodiment of FIG. 4, a bottom side of the parallel rods of the sample holder 13' can be fixed to an annular holding section 15 which seats beneath the sample 1 on the bottom side (see FIG. 2) thereof.

In embodiments which are not shown in the drawing, the gripping device 4 can be operated mechanically instead of magnetically or pneumatically. The geometric construction of the sample-sided parts of the gripping device 4 would be similar to that of the embodiments shown.

Figure 5:
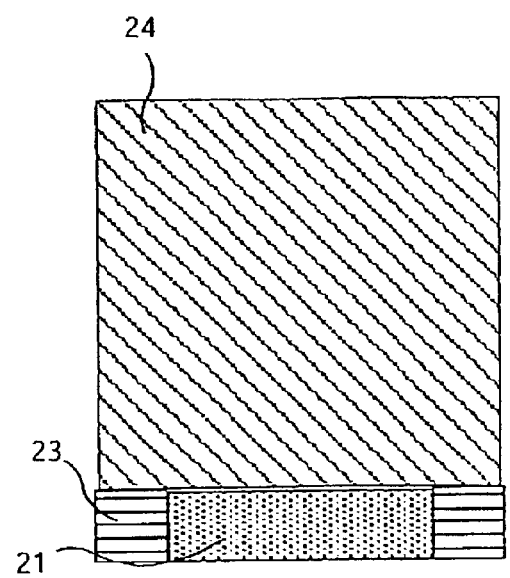
FIG. 5 shows a schematic vertical section through a gripping device including sample and sample ring according to prior art.

Finally, by way of comparison, FIG. 5 schematically shows a gripping device 24 according to prior art which grips a sample ring 23 with fitted sample 21 (also according to prior art). In contrast to the embodiment shown in FIG. 2, the sample 21 ends flush with the sample ring 23 in the z direction (FIG. 5). For this reason, the sample-sided end of the gripping device 24 is not designed to permit lateral gripping of projecting parts of the sample.

We claim:

1. An X-ray analysis apparatus for investigating a plurality of samples through automated exchange and transfer of those samples, the apparatus comprising:

a plurality of sample holders, each sample holder surrounding a held sample such that said held sample projects past said sample holder in a vertical z direction extending at right angles to a horizontal x-y plane; and a gripping device for precise transfer of any desired held sample from a depositing position to and from at least one of a transfer position and a measuring position, the gripping device being structured and disposed to surround parts of said held sample projecting past said sample holder in the z direction, wherein said gripping device comprises at least three parallel bars distributed about a periphery of said held sample, said bar extending in said z direction to engage said sample holder.

2. The X-ray analysis apparatus of claim 1, wherein said sample holder comprises at least one holding section disposed to support said held sample at a bottom side thereof in a plane extending parallel to said x-y plane for acting as a mechanical stop for said held sample in said in z direction.

3. The X-ray analysis apparatus of claim 2, wherein said holding section is annular.

4. The X-ray analysis apparatus of claim 1, wherein said sample holder surrounds a portion of said held sample facing said gripping device in one of an annular and a circular fashion.

5. The X-ray analysis apparatus of claim 1, wherein said sample holder comprises several parallel rods extending in said z direction to peripherally surround said held sample along a portion thereof facing said gripping device.

6. The X-ray analysis apparatus of claim 2, wherein said holding section is annular and said sample holder comprises several parallel rods disposed on an upper side of said annular holding section facing said gripping device said parallel rods extending in said z direction to peripherally surround said sample along a portion thereof facing said gripping device.

7. The X-ray analysis apparatus of claim 6, wherein said annular holding section comprises plastic material into which said rods are fitted on said side of said sample holder facing said gripping device, wherein said rods are ferromagnetic.

8. The X-ray analysis apparatus of claim 1, wherein said bars are evenly distributed about said periphery.

9. The X-ray analysis apparatus of claim 1, wherein said gripping device is operated magnetically.

10. The X-ray analysis apparatus of claim 9, wherein said gripping device is an electromagnet.

11. The X-ray analysis apparatus of claim 9, wherein a side of said sample holder facing said gripping device during operation, comprises at least one of magnetizable and ferromagnetic material.

* * * * *